US008747754B2

(12) United States Patent
Abate

(10) Patent No.: US 8,747,754 B2

(45) Date of Patent: Jun. 10, 2014

(54) BIPOLAR IONIZATION TUBE

(75) Inventor: Anthony M. Abate, Seymour, CT (US)

(73) Assignee: Clean Air Group, Inc., Fairfield, CT (US)

(*) Notice: Subject to any disclaimer, the term of this patent is extended or adjusted under 35 U.S.C. 154(b) by 560 days.

(21) Appl. No.: 12/742,749

(22) PCT Filed: Sep. 17, 2008

(86) PCT No.: PCT/US2008/011023

§ 371 (c)(1), (2), (4) Date: May 13, 2010

(87) PCT Pub. No.: WO2009/064334

PCT Pub. Date: May 22, 2009

(65) Prior Publication Data

US 2010/0247389 A1 Sep. 30, 2010

Related U.S. Application Data

(60) Provisional application No. 61/002,994, filed on Nov. 13, 2007.

(51) Int. Cl.
*A61L 9/20* (2006.01)

(52) U.S. Cl.
USPC .......................................... 422/121; 29/592.1

(58) Field of Classification Search
USPC ........................... 422/121; 361/231; 29/592.1
See application file for complete search history.

(56) References Cited

U.S. PATENT DOCUMENTS

| | | | | |
|---|---|---|---|---|
| 1,793,799 | A | 2/1931 | Hartman | |
| 7,120,006 | B2 * | 10/2006 | Sekoguchi et al. | 361/230 |
| 2007/0096081 | A1 | 5/2007 | Sugawara | |

FOREIGN PATENT DOCUMENTS

| | | | |
|---|---|---|---|
| CH | 666372 | A5 | 7/1984 |

* cited by examiner

*Primary Examiner* — Sean E Conley

(74) *Attorney, Agent, or Firm* — Abelman, Frayne & Schwab

(57) ABSTRACT

A bipolar ionization tube includes a cylindrical glass tube having an open end and closed end. A cathode is positioned within and is circumscribed by an interior surface wall of the glass tube. An anode circumscribes an exterior surface of the glass tube, where the anode is adapted for electrical connectivity with a first conducting terminal of a power supply. An electrically insulated end cap has a groove for receiving the open end of the glass tube, and the end cap is secured to the glass tube with at least one sealant. An elongated conducting terminal having a first portion extends through the end cap and is adapted for electrical connectivity with a second conducting terminal of the power supply. A second portion of the conducting terminal extends into the glass tube and is configured for electrical connectivity with the cathode.

18 Claims, 7 Drawing Sheets

BIPOLAR IONIZATION TUBE

CLAIM FOR PRIORITY

This application claims priority to PCT/US2008/011023, filed 17 Sep. 2008, which claims benefit to U.S. Provisional Patent Application No. 61/002,994, filed on 13 Nov. 2007.

BACKGROUND OF THE INVENTION

1. Field of the Invention

The present invention relates generally to air purifiers, and more specifically to bipolar ionization tubes for use in heating, ventilation and cooling (HVAC) systems to reduce the number of air particulates.

2. Description of the Related Art

Indoor air environments frequently include suspended particulates, such as dust, dander, soot and smoke particles, pollen, mold, bacteria, and viruses. Indoor gases are also present, being released from building materials, home furnishings and nondurable goods. In office environments, the greater user of machines, such as photocopying equipment and the like, is especially problematic, as this equipment may emit volatile organic compounds.

These particulates can degrade the quality of the air, making it less pleasant and even dangerous to occupants of the space. Modern construction techniques that promote energy efficiency, such as insulating walls, ceilings, doors and windows, and wrapping buildings with air intrusion barriers, have created spaces that are so airtight that the buildings are unable to off-gas toxic elements.

In ordinary heating, ventilation and cooling (HVAC) systems, air is drawn through a filter, which is intended to trap particulates in the filter. However, traditional filters are only effective for large particles of at least 10 microns in size. While high efficiency particle air (HEPA) filters are more effective, they also have disadvantages, as they may quickly become clogged, requiring frequent changing to avoid overburdening the HVAC equipment. Because of the presence of contaminants in the air and the general inability of physical filters to remove the same, a condition known as "sick building syndrome" has developed. Various building codes designed to mitigate this syndrome have been introduced; for example, the American Society of Heating, Refrigeration & Air Conditioning Engineers (ASHRAE) recommends a minimum of 8.4 air exchanges in a 24-hour period (a 35% turnover rate). While commercial and industrial facilities generally meet that minimum level, their air quality may remain inferior. Furthermore, there are many houses that do not even meet such minimum levels. While greater turnover rates would increase the interior air quality, they would also reduce the buildings' energy efficiencies.

An alternative method to filtering involves the use of ion exchange technology to remove contaminants from air. Ionization occurs where an atom or group of atoms loses or gains one or more electrons. An electrically neutral atom or molecule will have an equal number of electrons and protons. If an electron bound to an atom or molecule absorbs enough energy from an external source, it may exceed the ionization potential and allow the electron to escape its atomic orbital. When this occurs, the electron is lost, and an ion with a positive electrical charge, a cation, is produced. Electrons that are lost become free electrons. When a free electron later collides with an atom, it may be captured within an orbital. The gain of an electron by an atom or molecule creates an ion with a negative electrical charge, an anion.

The ionization of air, e.g., air in the Earth's atmosphere, results in the ionization of the air's constituent molecules, primarily oxygen and nitrogen. While the nitrogen in air is more plentiful than oxygen, oxygen is more reactive. Thus, oxygen has a lower ionization potential than nitrogen, allowing for oxygen cations to be formed with greater ease than nitrogen cations, and oxygen has a higher electro-negativity than nitrogen, allowing for oxygen anions to be formed with greater ease than nitrogen anions.

Ionization is known to break down organic chemicals into the basic molecular constituents of water, carbon dioxide, and related metal oxides. Thus, ionization has potential for cleaning indoor air, by eliminating organic molecules and their associated odors from the enclosed environment. Ionization also contributes to the reduction of inorganic pollutants, by imparting a charge to those molecules, which clump together and then drop out of the air.

Studies indicate that positive ions (cations) may impair human health in a number of ways, such as by stimulating increased production of the neurohormone serotonin, which may lead to exhaustion, anxiety and depression. Positive ions are frequently found in offices where VDUs (visual display units) are used. Negative ions (anions) have a calming effect. Thus, a machine that cleans indoor air should seek to introduce negative ions into the airstream.

Various commercial products have been made including machines that incorporate bipolar ionization tubes. The ionization of air may also produce ozone, $O_3$, which is not desirable. Therefore, there is demand for a system which provides a sufficient level of ionization to effectively address the contaminants in an airstream, while minimizing the production of ozone.

Under the circumstances, it would be highly desirable to use ion exchange technology for air treatment, and indeed there are many suppliers of bipolar ionization tubes that are stand alone devices used in specified locations, or centralized installations which are integrated into a building HVAC system. These devices are used in a way so that air circulated into and recirculated within the building can pass over the bipolar emitting devices, which generally take the form of an ionization tube or tubes. This would accomplish the goal of improving air quality, without mandating greater air exchange rates. Thus, an additional benefit of ionization treatment of indoor air is that it contributes to the efficiency of HVAC operations.

In U.S. Pat. No. 1,793,799, issued to Hartman, a bipolar ionization tube is disclosed having a cathode formed by a metallic lining located along an interior surface of a glass tube. While the '799 patent discloses a wire mesh forming the anode, it does not suggest the use of a comparable wire mesh as the cathode. Rather, the '799 patent disclosed that the interior of a vacuum pumped glass tube be treated with the application, by brush, of a finely divided metal mixed with an adhesive. Neither the brushing and vacuum requirements are desirable manufacturing steps and the degree and interstitial spacing of the metal is random.

There is also a commercially available product sold under the Bentax™ trademark, which employs a tube assembled without vacuum pumping, and which uses a wire mesh for the cathode. It includes an open ended tube which is separately closed with an end cap. Although addressing some of the deficiencies of Hartman's bipolar ionization tube, the Bentax™ tubes are relatively fragile, have encountered numerous mechanical failures during shipping and due to mishandling, and stress-related failures at temperatures above 140° F.

Therefore, there is a need in the art for an improved, more efficient bipolar ionization tube with lower manufacturing costs, a reduced mechanical failure rate, and which can as a result be reduced in size and therefore be better adapted for installation in a wider range of HVAC systems or stand-alone devices.

BRIEF SUMMARY OF THE INVENTION

The present invention discloses a bipolar ionization tube for use with heating, ventilation and cooling (HVAC) systems and stand-alone devices, and providing lower manufacturing costs, a reduced mechanical failure rate, higher efficiency, and in view of the higher efficiency can, if desired, be reduced in size. In one embodiment, the bipolar ionization tube includes a cylindrical glass tube having an open end and closed end. A cathode is positioned within and is circumscribed by an interior surface wall of the glass tube. An anode circumscribes an exterior surface of the glass tube, where the anode is adapted for electrical connectivity with a first conducting terminal of a power supply.

In one embodiment, the anode is fabricated from stainless steel in a form of a tightly woven mesh or grid having a plurality of interstitial spaces or perforations of approximately 180 to 290 openings per square inch. Additionally, the cathode is fabricated from aluminum stretch metal and also in the form of a mesh or grid having a plurality of interstitial spaces or perforations of approximately 180 to 290, openings per square inch. In one embodiment, the anode and cathode include approximately 225 openings per square inch.

An electrically insulated end cap is provided to cover the open end of the glass tube. The end cap includes a groove for receiving the peripheral edge at the open end of the glass tube, and the end cap can be secured to the glass tube with at least one sealant, such as a two-part epoxy. An elongated conducting terminal having a lower portion extends through the end cap and is adapted for electrical connectivity with a second conducting terminal of the power supply.

A second portion of the conducting terminal extends into the glass tube and is configured for electrical connectivity with the cathode. In one embodiment the upper end of the conducting terminal includes a current distributor having a plurality of tines that extend a length to contact adjacent portions along the inner surface of the cathode.

In yet another embodiment, a method for fabricating the ionization tube includes providing a cylindrical glass tube having an open end and closed end, providing an end cap having a groove sized to receive a peripheral edge of the open end of the glass tube, and providing a conducting terminal having a current distributor and a cathode lead.

A cylindrical cathode, such as a stretch aluminum metal cathode having interstitial spacing or perforations of approximately 180 to 290 openings per square inch is inserted into the glass tube. In one embodiment, the cathode includes 225 openings per square inch. A lower end of the conducting terminal is secured to the end cap, and the glass tube is placed over the conducting terminal and slid downward towards the end cap such that the peripheral edge of the open end of the glass tube is seated within the groove of the end cap.

In one embodiment a second sealant is applied around the upper edge of the end cap and the adjacent exterior wall of the glass tube. In yet another embodiment, a third sealant is provided at the lower end of the conducting terminal. The sealants provide additional structural support and help prohibit contaminants from entering the glass tube.

A cylindrical anode is positioned about the circumference of the glass tube. In one embodiment, the anode is fabricated from stainless steel and formed as a tightly woven grid having interstitial spaces or perforations of approximately 180 to 290 perforations per square inch.

The ionization tube is adapted for mechanical and electrical connectivity to an AC power supply. In one embodiment, the conducting terminal includes a power input terminal extending from the bottom surface of the end cap for providing current to the cathode via the current distributor. A stainless steel clip or wire from a second terminal of the power supply can be coupled to the anode to complete the circuit.

BRIEF DESCRIPTION OF THE DRAWINGS

Further advantages and features of the present invention will become apparent from the detailed description of a preferred embodiment of the invention with reference to the accompanying drawings, in which.

Figure 1:
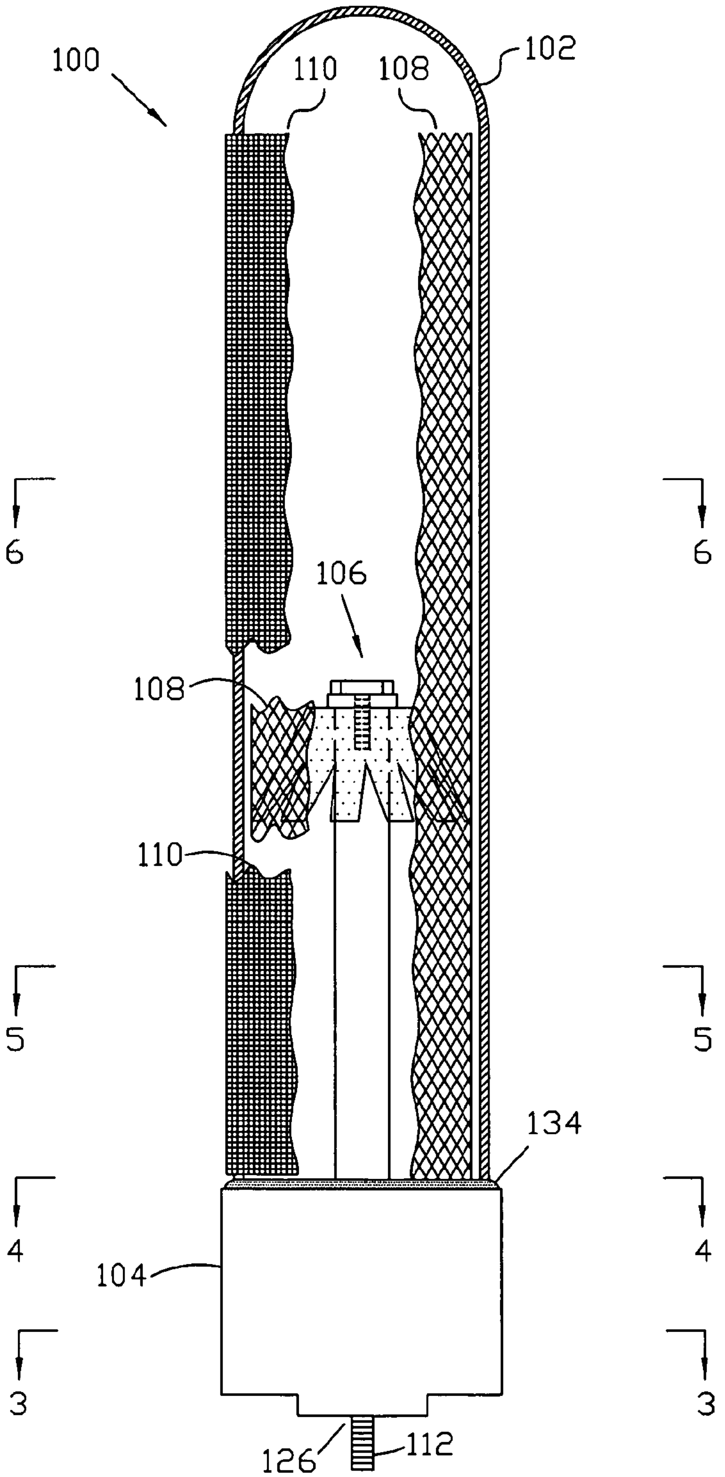
FIG. 1 is an elevated view of a bipolar ionization tube in accordance with the present invention.

To facilitate understanding of the invention, identical reference numerals have been used, when appropriate, to designate the same or similar elements that are common to the figures. Further, unless stated otherwise, the drawings shown and discussed in the figures are not drawn to scale, but are shown for illustrative purposes only.

DETAILED DESCRIPTION OF THE INVENTION

The present invention is a bipolar ionization tube for removing impurities, such as dust, pollen, mold, compounds producing noxious odors, among other undesirable particles from the air, that manifest themselves, illustratively, in ventilation systems of buildings, although such environment is not considered as being limiting.

Among the improvements in the tube of the present invention is the improvement in overall structural integrity. Thus, in one embodiment, the peripheral edge of the open end of the glass tube is rounded or beveled (e.g., by an annealing process) to reduce stresses originating at the edge of the open end of the glass tube. In another embodiment, the interior floor of the end cap is formed with a groove to provide support for the end (i.e., peripheral edge) of the glass tubes, thereby enhancing overall tube fit and strength.

In yet another embodiment, the glass tube is secured to the end cap with at least one sealant. In particular, a first sealant, such as a two-part epoxy, is applied to the groove formed in the interior floor of the end cap, prior to receiving the open end of the glass tube, and the unit is then heat cured. A second sealant, such as a one-part silicon rubber, is applied to the outer joint where the glass tube enters the end cap. Not only is the structural integrity improved, the range of safe operating temperatures is increased from 140° F. to 200° F., without mechanical failures induced by expansions and contractions between the glass tube and end cap due to temperature changes in the environment.

The improved tube provides for an anode and cathode which increase the ion output of the ionization tube. In one embodiment, aluminum stretch metal is utilized to form the cathode. Slits are cut in a metal foil, and the metal foil is then stretched in a direction perpendicular to the longitudinal direction of the slits, to thereby form a net with rhombic meshes. The result is more perforations per square inch than is achievable through the prior art die cutting methods. As a result of the greater number of perforations per square inch, there is increased surface area or points where ions can be produced.

In a preferred embodiment, the outer stainless steel mesh used to circumscribe the glass tube and form the anode is fabricated with a tightly woven mesh, which allows for more contact points to produce ions. Although having the anode mesh contacting the tube has been known, the ability to tighten the mesh into greater contact was limited by the structural integrity of the tube. In accordance with the present invention a more intimate fit is permitted. As a result of the combination of the improvements to the cathode and anode, there is an average 30% increase in ion output when compared to prior art tubes of similar size. In addition to other benefits, by reducing the number or bipolar ionization tubes placed into an airstream, or by using a tube of a smaller size that is able to produce as much ionization as a larger tube, there will be a reduction in the resistance to airflow, allowing for a more efficient HVAC system.

Reference will now be made in detail to implementations of the invention, examples of which are illustrated in the accompanying drawing.

FIG. 1 illustrates an embodiment of a bipolar ionization tube 100 of the present invention. The bipolar ionization tube 100 includes a glass tube 102, an end cap 104, a conducting terminal 106, a cathode 108, an anode 110, and at least one sealant, such as first sealant 130 and/or second sealant 132 for securing the end cap 104 to the glass tube 102. Optionally, a third sealant 134 can be provided to secure the conducting terminal 106 to the end cap 104.

The glass tube 102 has an elongated cylindrical shape, with a wall of substantially uniform cross-section, forming an interior surface and an exterior surface. The glass tube 102 has a first end and a second end. The first end is closed, with a rounded U-section. The second end is open, with edges that are annealed to form a rounded or beveled peripheral edge 150 to reduce stresses that may occur with a rough cut or unfinished peripheral edge. In one embodiment the outer diameter of the glass tube can be approximately 1.0 to 1.75 inches, and is preferably about 1.375 inches. The overall length of the glass tube can be about 7 inches to 21 inches, although such lengths are not considered limiting. The thickness of the glass wall forming the tube 102 is preferably 0.031 inches. A person of ordinary skill in the art will appreciate that the dimensions of the glass tube 102 are associated with the desired overall ion output and are not considered as limiting. The edge 150 at the open end of the glass tube 102 is seated in a groove 124 formed along an interior floor 122 of the end cap 104.

Arranged against the inner wall of the glass tube 102 is the cathode 108. Preferably, the cathode 108 (shown broken for sake of clarity in FIG. 1) is formed from stretch aluminum and is cylindrical in shape. Although the cathode 108 is described as being fabricated from aluminum, a person of ordinary skill in the art will appreciate that other conductive metals or metal alloys can be utilized to form the cathode 108, such as stainless steel, and the like.

The cathode 108 is sized to cover the interior surface of the glass tube 102, from the beginning of the curved portion at the closed end to within, for example, about ¼" of the edge 150 of the open end of the glass tube 102, allowing enough space at the edge 150 of the glass tube 102 so that the edge 150 of the glass tube 102 may properly fit into the groove 124 formed in the floor 122 of the end cap 104. The cathode 108 extends the length of the glass tube 102 and terminates approximately where the inwardly curving U-shaped end begins to form. In a preferred embodiment, the cathode 108 has a thickness of approximately 0.010 inches, and 225 openings per square inch. Alternatively, the cathode 108 can have a thickness in the range of 0.008 to 0.013 inches, and 180 to 290 openings per square inch.

The length of the cathode 108 is dependent on the length of the glass tube 102. For example, a cathode having a length of approximately 5 inches is used with a glass tube having an overall length of 7 inches; a cathode having a length of approximately 7 inches is used with a glass tube having an overall length of 9.5 inches; a cathode having a length of approximately 12 inches is used with a glass tube having an overall length of 14 inches; and a cathode having a length of approximately 18.5 inches is used with a glass tube having an overall length of 21 inches. The lengths of the cathodes can be increased by approximately 0.25 inches for the above-mentioned glass tube lengths.

The anode 110 (also shown broken for sake of clarity in FIG. 1) is arranged on the outer wall of glass tube 102. The anode 110 is cylindrical in shape and fabricated from a stainless steel mesh, which covers the exterior surface of the glass tube 102, from the beginning of the curved portion at the closed end to where the glass tube meets the end cap 104. Although the anode 110 is described as being fabricated from stainless steel, a person of ordinary skill in the art will appreciate that other conductive metals or metal alloys can be utilized to form the cathode 108, such as aluminum, and the like.

In a preferred embodiment, the anode 110 has a thickness of approximately 0.14 inches, and 225 openings per square inch. Alternatively, the anode 110 can have a thickness in the range of 0.01 to 0.015 inches, and 180 to 290 openings (i.e., perforations) per square inch.

Similar to the cathode 108, the length of the anode 110 is also dependent on the length of the glass tube 102. Preferably, the anode 110 is approximately the same or slightly larger that the length of the cathode 108. Preferably, the anode 110 does not extend beyond the rounded closed end of the glass tube 102, although performance will not be affected if the anode does extend beyond the rounded closed end and the anode 110 and cathode 108 are properly aligned. In one embodiment, an anode having a length of approximately 6 inches is used with a glass tube having an overall length of 7 inches; an anode having a length of approximately 8 inches is used with a glass tube having an overall length of 9.5 inches; an anode having a length of approximately 12.5 inches is used with a glass tube having an overall length of 14 inches; and an anode having a length of approximately 19.5 inches is used with a glass tube having an overall length of 21 inches. The lengths of the anodes 110 can be increased by approximately 2.0 inches for the above-mentioned glass tube lengths without degradation in performance.

The anode 110 is electrically connected to a high-voltage alternating current power supply with an electrical conductor (not shown), such as a stainless steel clip, wire, or other well-known electrical conductor. In one embodiment, a stainless steel clip extends from the positive lead of the power supply and is positioned to securely contact the outer surface area of the anode 110.

Figure 2:
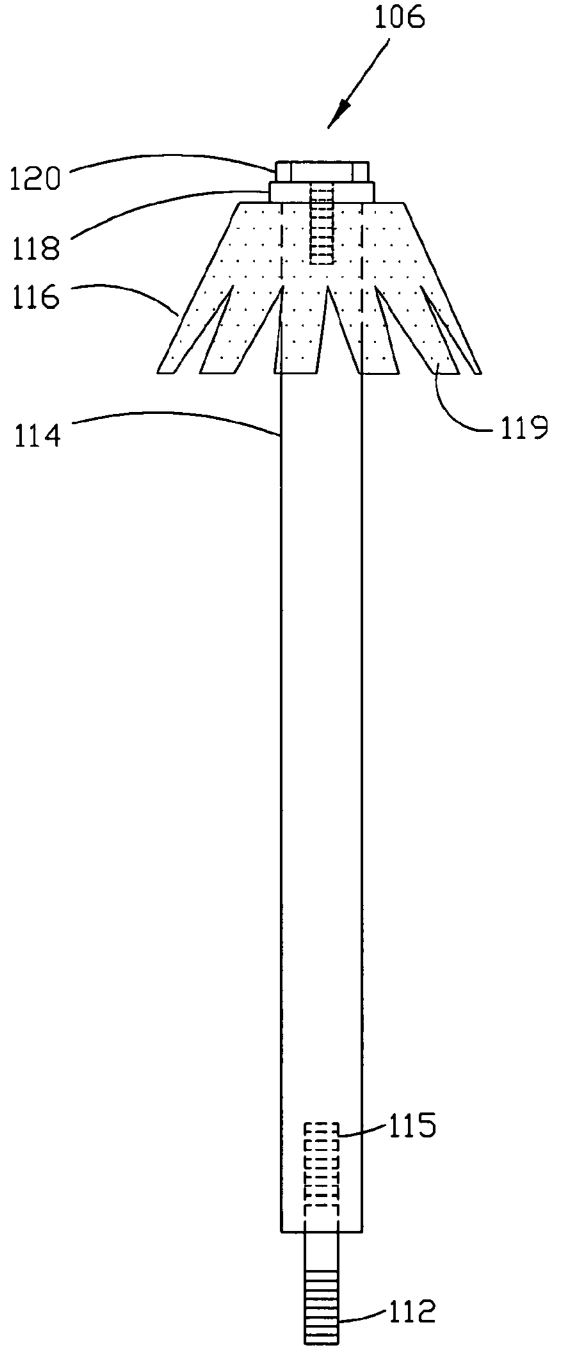
FIG. 2 is an elevated view of a current distributor of the ionization tube of FIG. 1.
Figure 5:
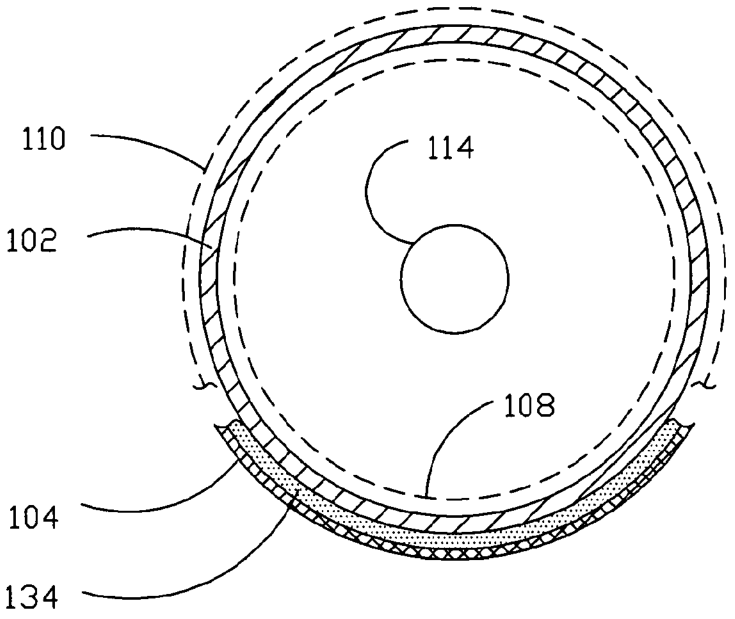
FIG. 5 is a cross-sectional view of a lower portion of a glass tube of the ionization tube taken along lines 5-5 of FIG. 1.

Referring now to FIGS. 2 and 5, FIG. 2 shows an elevated view of the conducting terminal 106 and FIG. 5 illustrates the positioning of the conducting terminal 106 relative to the cathode 108 in the glass tube 102. The conducting terminal 106 includes a power input terminal 112, a cathode lead 114, a current distributor 116, and a fastener, such as a bolt 120 and washer 118 for securing the current distributor 116 to the cathode lead 114.

The power input terminal 112 is made of a conductive metal, such as copper. The power input terminal 112 extends through a bore 128 formed through the floor 122 of the end cap 104. Within the end cap 104, the power input terminal 112 is mechanically and electrically connected to the cathode lead 114. In one embodiment, the bottom portion of the cathode lead 114 includes a threaded bore 115 sized to receive a threaded end of the power input terminal 112. Alternatively, other techniques for fastening the power input 112 to the cathode lead 114 can be implemented, such as by welding, by inserting a pin, and the like.

The power input terminal 112 extends a sufficient length from the external surface of the bottom portion of the end cap 104 to allow for connection to the separate high-voltage alternating current power supply. The external end of the power input terminal 112 can be a threaded, as illustratively shown in FIG. 1, although such terminal connector is not considered as limiting. For example, the power input terminal 112 can be of a plug-in or stab-on type connector, amongst other well-known connectors.

The cathode lead 114 is shaped as an elongated rod and fabricated from a conductive metal, such as stainless steel to provide electrical conductivity to and mechanical support for the current distributor 116. Alternatively, the cathode lead 114 can be fabricated from aluminum, copper, among other conductive metals or metal alloys.

The current distributor 116 is made of a conductive metal, such as stainless steel, aluminum, and the like. The current distributor 116 has at least eight and preferably twelve engagement ribs or tines 119 that extend radially outward, such as in a starburst design. As shown in FIG. 2, the tines 119 are sloped downward towards the lower end of the cathode lead 114 to enable the glass tube 102 to be easily inserted over the current distributor 106 after the current distributor 106 is attached to the end cap 104.

Figure 6:
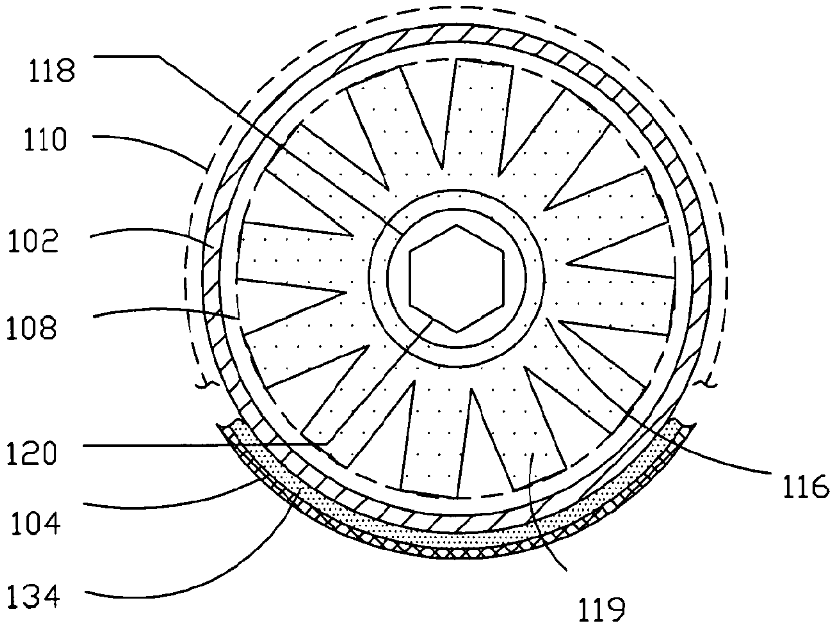
FIG. 6 is a cross-sectional view of an upper portion of the glass tube of the ionization tube taken along lines 6-6 of FIG. 1.

Referring to FIG. 6, the tines (e.g., 12 tines) extend a length to provide continuous contact at coincidental points along the inner surface of the cathode 108. The current distributor is fastened to the cathode lead 114. Although different methods of fastening may be used, such as welding or screws in various configurations, an exemplary fastening technique is shown in FIG. 2, in which the current distributor 116 is secured to the cathode lead 114 with a washer 118 and bolt 120.

Figure 7:
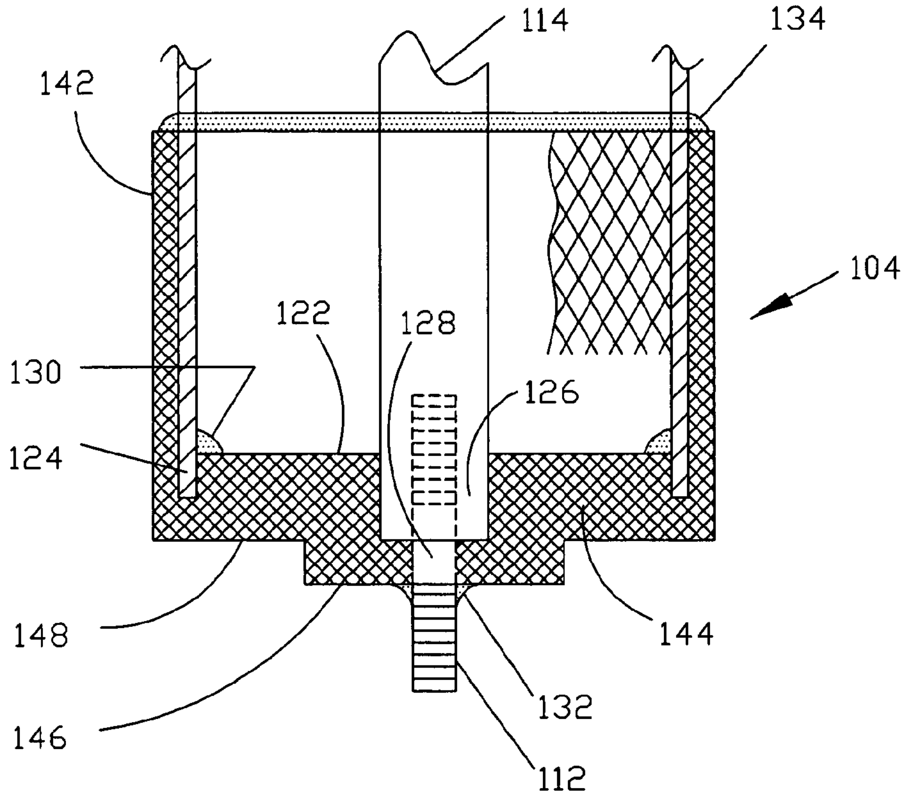
FIG. 7 is a cross-sectional view of the end cap of the ionization tube taken along lines 7-7 of FIG. 4.

FIG. 7 is a sectional view of the end cap 104, which is fabricated from a rigid electrical insulator, such as chlorinated polyvinyl chloride (CPVC). Other materials that can be used to form the end cap 104 can include polyvinyl chloride (PVC) and the like. The end cap 104 includes a cylindrical side wall 142 and a bottom portion 144 such that the end cap has an open end and an opposing closed end formed by the bottom portion 144. A circular protrusion 146 having a diameter less than the diameter of the side wall 142 extends coaxially from the external surface 148 of the bottom portion 144. As described below in further detail, the bottom portion 144 and protrusion 146 have a thickness suitable for receiving the peripheral edge 150 of the glass tube 106, the cathode lead 114, and the power input connector 112.

The interior diameter of the end cap 104 is sized to receive the exterior walls of the glass tube 102 such that the external surface proximate the open end of the glass tube 102 is in contact with the interior surface of the side wall 142. A groove 124 is formed along the interior surface of the bottom portion 144 adjacent to the interior surface of the side wall 142. Accordingly, the interior surface of the side wall 142 forms an outermost wall of the groove 124. The groove 124 is sized and shaped to receive the peripheral edge 150 of the open end of the glass tube 102.

Figure 3:
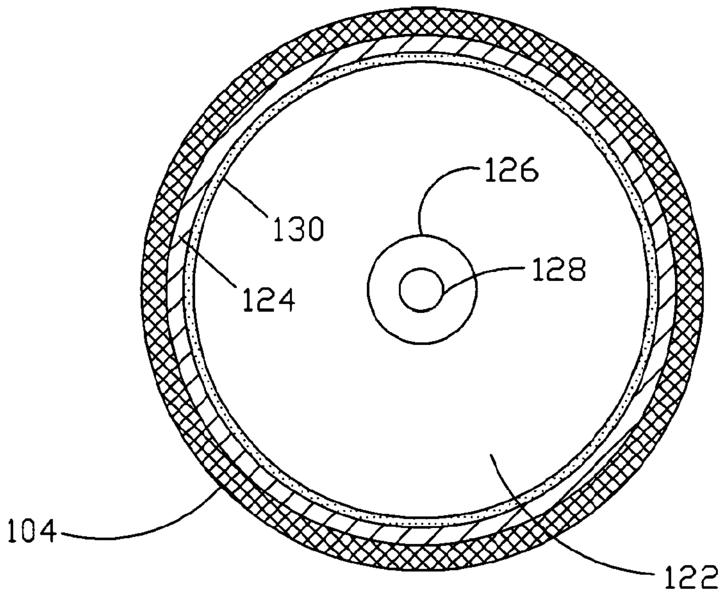
FIG. 3 is a cross-sectional view of a lower portion of an end cap of the ionization tube taken along lines 3-3 of FIG. 1.

Referring to FIGS. 3 and 7, a recess 126 is formed in the center of the interior surface of the bottom portion 144 and is sized and shaped to receive a lower portion of the cathode lead 114. A bore 128 having a diameter less than the diameter of the recess 126 is coaxially formed through the center of the protrusion 146 and extends to and adjoins the recess 126. The bore 128 is configured to receive the power input terminal 112, which is fastened to the lower end of the cathode lead 114, as described above.

Accordingly, the groove 124 provides a seat for the peripheral edge 150 of the open end of the glass tube 102. Similarly, the recess 126 provides a seat for the lower end of the cathode lead 114, and the bore 128 securely retains the conducting power input terminal 112.

In one embodiment, a first sealant 130, such as a two-part epoxy, is placed within the groove 124 of the end cap 104, immediately prior to the placement of the glass tube 102 within the end cap 104 and the subsequent seating of the open end of the glass tube 102 within the groove 124 of the end cap 104. In one embodiment, the two-part epoxy is rated for temperatures conditions between −300° F. to +600° F.

Figure 4:
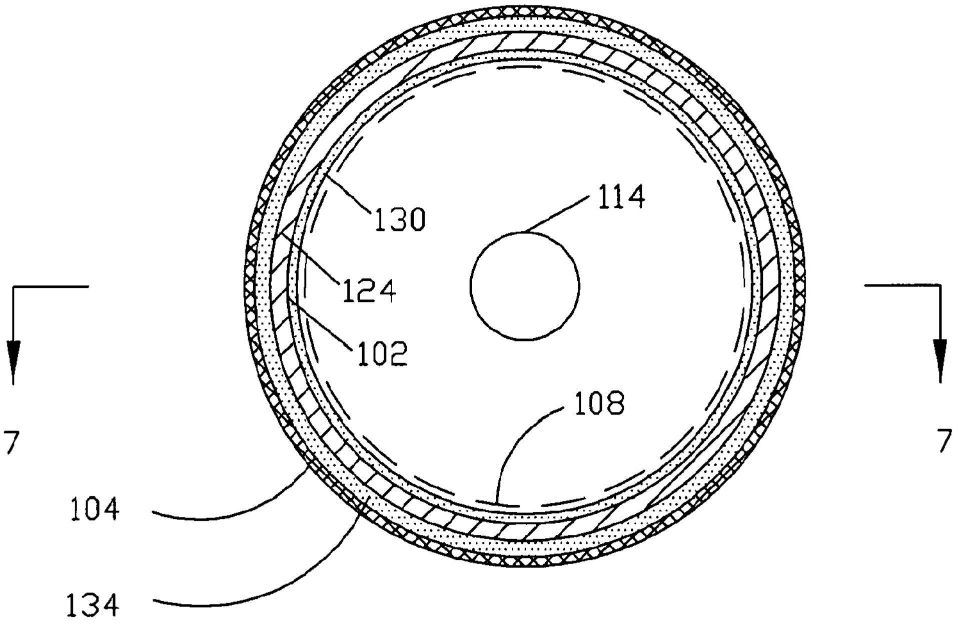
FIG. 4 is a cross-sectional view of an upper portion of the end cap of the ionization tube taken along lines 4-4 of FIG. 1.

As shown in FIGS. 4 and 7, the first sealant 130 is provided within the groove 124 and preferably forms a bead circumscribing the floor 122 of the bottom portion 144 and the adjacent interior wall proximate the peripheral edge 150 of the glass tube 102. The first sealant 130 serves to permanently seat and secure the peripheral edge 150 at the open end of the glass tube 102 to the end cap 104, and also to prevent contaminants from entering the glass tube 102.

A second sealant 132, such as a two-part epoxy, can be used to seal the power input terminal 112 within the bore 128, as well prevent outside contaminants from entering through the bore 128 of the end cap 104. In one embodiment, the two-part epoxy is the same as the first sealant 130 having a rating for temperature conditions between −300° F. to +600° F. Referring to FIG. 1, the second sealant is shown disposed at the joint circumscribing the terminal 112 and the bore 128 formed along the bottom surface of the protrusion 146 of the end cap 104.

A third sealant 134, such as a one-part silicon rubber, can be used to seal the outer joint of the end cap 104 to the glass tube 102. In one embodiment, silicon rubber sealant is rated for temperature conditions up to +400° F.

As shown in FIG. 7, the third sealant 134 preferably forms a bead at the joint circumscribing upper edge of the side wall 142 of the end cap 104 and the adjacent exterior surface of the glass tube 102. The third sealant 134 provides additional joint strength between the end cap 104 and glass tube 102, and additional protection from outside contaminants.

Figure 8A:
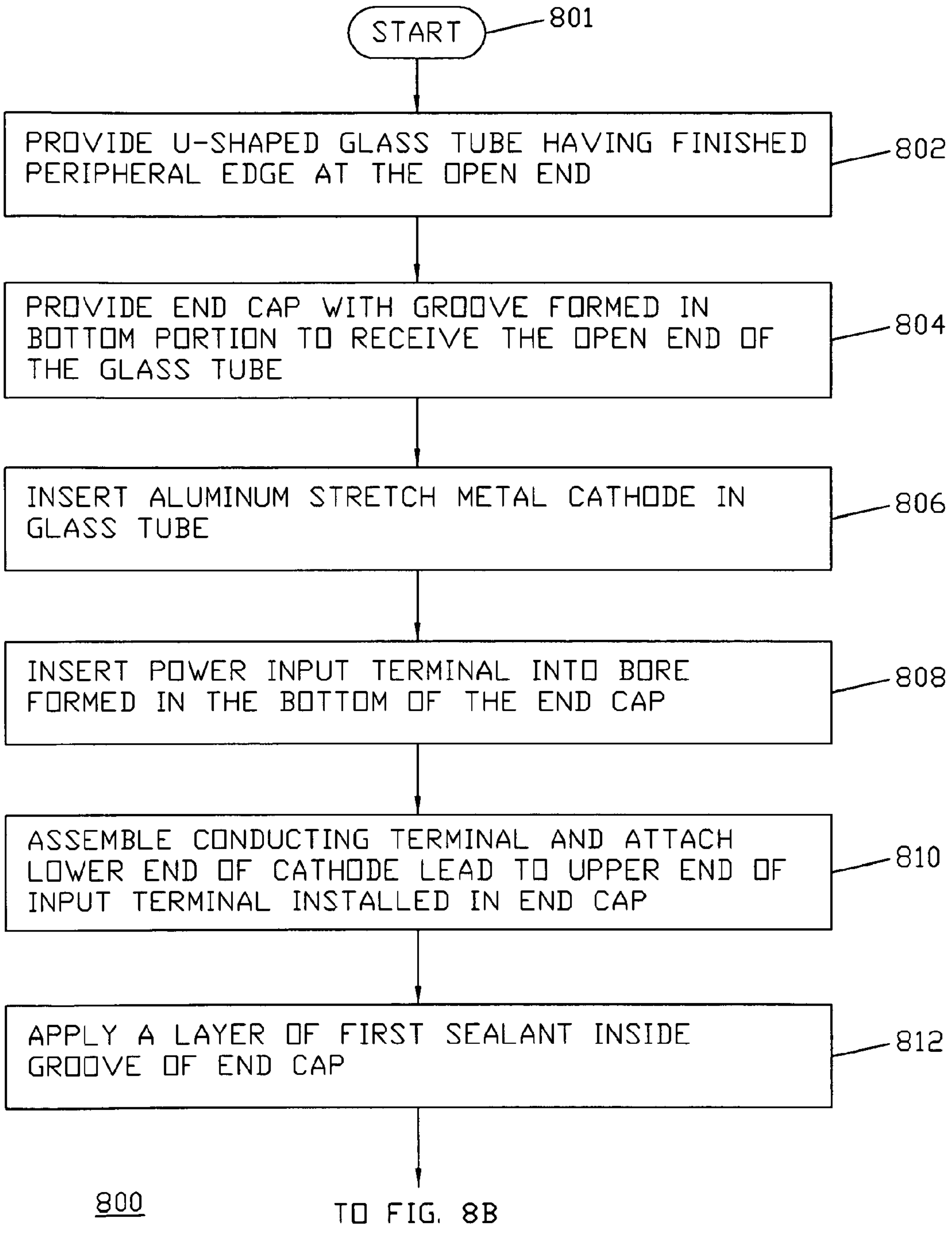
FIGS. 8A and 8B collectively provide a flow diagram of a method for fabricating the bipolar ionization tube of the present invention.
Figure 8B:
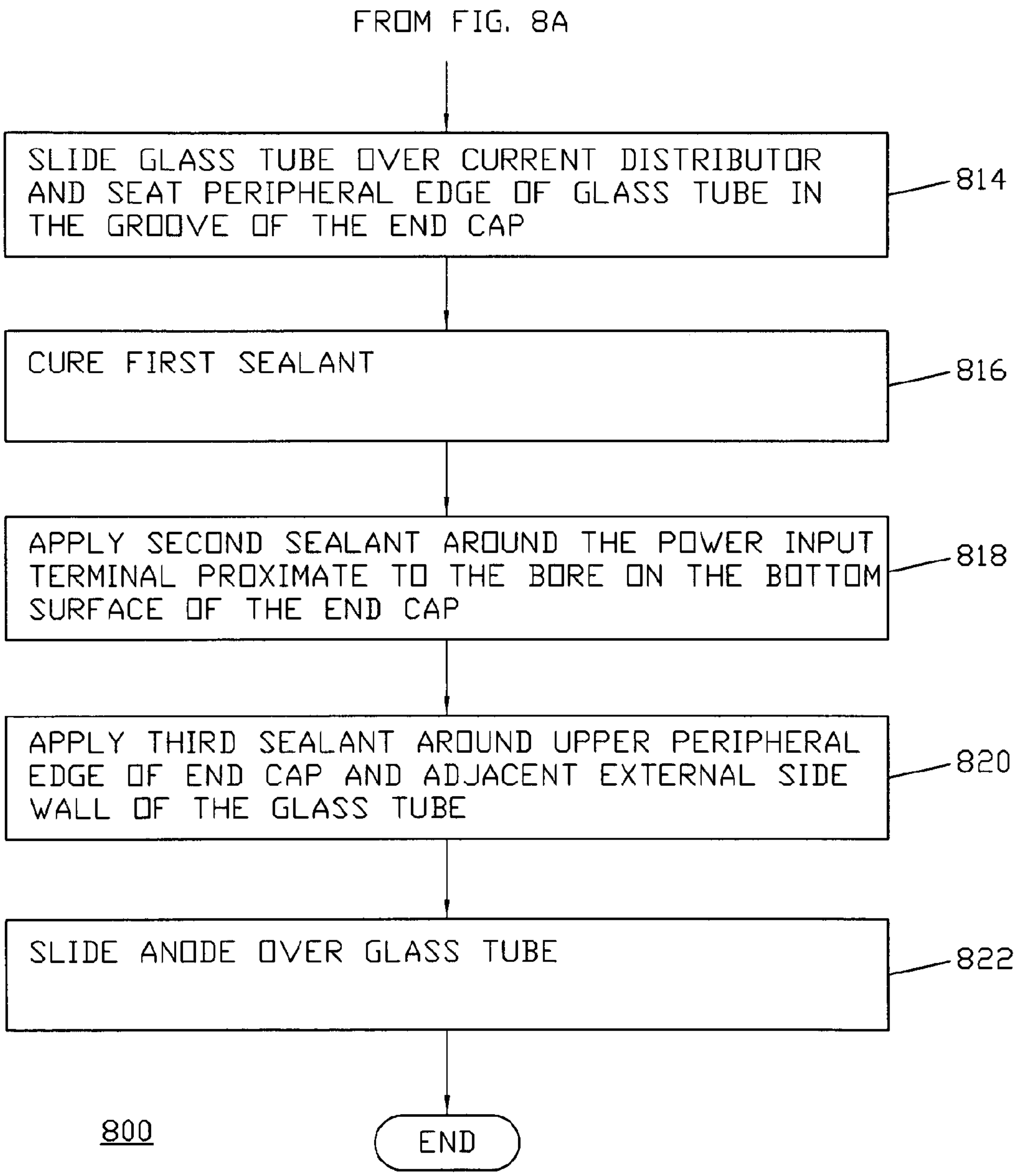

Referring to FIGS. 8A and 8B, a method 800 for fabricating the ionization tube 100 of the present invention is illustratively shown in the flow chart. The method 800 starts at 801 and proceeds to step 802, where the U-shaped glass tube 102 having a finished (e.g., rounded or beveled) peripheral edge 150 is provided. At step 804, an electrically insulated end cap

104 having a groove 124 formed in the bottom portion 144 to receive the peripheral edge 150 of the glass tube 102 is provided.

At step 806, the stretch aluminum metal cathode 108 is inserted into the interior of the glass tube 102. The cathode 108 is positioned such that the upper edge of the cathode 108 is proximately adjacent to the inwardly curved portion of the closed end begins to form its U-shaped end.

At step 808, the power input terminal 112 is inserted into the bore 128 formed in the bottom portion 144 of the end cap 104. In one embodiment, the bore 128 is sized to form-fit and tightly secure the power input terminal 112 therein. Alternatively, a sealant such as the sealant 132 described above can be applied to the inner walls of the bore 128 prior to inserting the input terminal 112.

At step 810, the conducting terminal 106 is assembled. In particular, the current distributor 116 is fastened to the upper end of the cathode lead 114, illustratively by a washer and a bolt, as described above. The lower end of the cathode lead 114 is attached to the upper end of the power input terminal 112, which is installed in the end cap 104. As shown in the figures, the cathode lead 114 is screwed onto the threaded upper end of the power input terminal 112, although other fastening techniques can be utilized as discussed above.

At step 812, a sealant 130, such as a two-part epoxy is applied to the inner walls and bottom of the groove 124 formed in the end cap 104. Depending on the type of sealant, the sealant can be allowed to partially cure prior to proceeding to step 814. At step 814, the glass tube 102 is slid over the conducting terminal 106 and slid downwards towards the end cap 104 until the peripheral edge 150 of the tube 102 is seated in the groove 124. The downward sloping tines 119 of the current distributor 116 prevent tearing or catching of the perforations of the cathode 108 when sliding the glass tube 102 over the conducting terminal 106. The method 800 then proceeds to step 816, where the sealant 130 is allowed to cure.

At step 818, a second sealant 832 is applied around the exposed power input terminal 112 proximate the bore on the bottom portion 144 of the end cap 104. The sealant 132 does not cover the terminal end of the input terminal 112. Rather, the sealant 132 is used to ensure that there is no open gap formed between the inner walls of the bore 128 and the adjacent terminal 112.

At step 820, a third sealant 834 is applied at the joint between the upper edge of the end cap 104 and the adjacent external wall of the glass tube 102. The sealant 834 is applied to provide additional structural support to the tube and prohibit any contaminants from entering the tube.

At step 822, the cylindrical stainless steel mesh anode 110 is slid over the upper end of the glass tube 102. The upper and lower edges of the anode 110 are aligned to coincide with the respective upper and lower edges of the cathode 108. The method 800 then proceeds to step 899, where the method ends and any additional curing of the sealants and testing of the assembled ionization tube is provided.

A person of ordinary skill in the art will appreciate that the specific order of the steps of method 800 is not considered limiting. For example, the insertion of cathode 108 into the tube 102 at step 806, the insertion of the input terminal 112 into the bore 128 of the end cap 104 at step 808, and the assembly of the conducting terminal 106 of step 810 can be performed in any order or contemporaneously. Additionally, the application of the sealants 832 and 834 can be performed in any order. Moreover, the curing steps are applicable only where curing of a particular sealant is required.

The bipolar ionization tube 100 can be installed, for example, in a heating, ventilation and cooling (HVAC) duct. During operation, the bipolar ionization tube is connected to a suitable power source, such as an AC power supply, which provides current to the power input terminal 112. The current flows across the cathode lead 114 and is distributed to the cathode 108 by the current distributor 116 through its tines 119. A conductive wire or clip is provided between the anode and the opposite charged terminal of the power source to complete the circuit.

Many of the electrons flowing from the cathode 108 are not collected by the oppositely charged anode 110. Rather, the electrons that escape through the interstices of the grid of the anode 110 migrate into the area surrounding the bipolar ionization tube 100 and generate a corona. As the electrons in the corona collide with air molecules and particulates in the air stream, they ionize them. Ionization of the air helps clean the air by breaking down organic chemicals and removing their associated odors, as well as reducing the levels of inorganic pollutants.

It is noted that the design of the anode and cathode, which includes the metals used for fabrication, as well as the increase in the number of perforations per square inch of the stretch aluminum metal cathode and the stainless steel anode mesh, are specifically directed towards increasing the ionization output the surrounding air over the prior art. Advantageously, energy costs to operate the ionization tube 100 of the present invention can be reduced as compared to the tubes of the prior art, since the enhancements to the anode and cathode increase the overall ion production of the tube 100.

Further advantages of the present invention include structural improvements to reduce mechanical stresses that may occur during handling and operation of the tube 100. In one embodiment, the peripheral edge of the open end of the tube is rounded or beveled to prevent stress cracks from originating at the edge. Further, a groove is provided in the end cap to receive and secure the peripheral edge of the tube. Sealants can also be provided, for example, between the groove and the peripheral edge of the open end of the tube, at the joint formed about the upper edge of the end cap and the adjacent exterior wall of the glass tube, and at the joint formed by input terminal and the bottom of the end cap to thereby enhance tube durability, for example, during shipping, handling, and operation in various environments.

Although an exemplary description of the invention has been set forth above to enable those of ordinary skill in the art to make and use the invention, that description should not be construed to limit the invention, and various modifications and variations may be made to the description without departing from the scope of the invention, as will be understood by those with ordinary skill in the art, and the scope thereof is determined by the claims that follow.

What is claimed is:

1. A bipolar ionization tube, comprising:

a cylindrical glass tube that is formed with an open end and closed end, the open end being annealed to form a rounded or beveled peripheral edge;

a wire mesh cathode positioned within and being circumscribed by an interior surface wall of said glass tube;

an anode circumscribing an exterior surface of said glass tube, said configured for electrical connectivity with a first conducting terminal of a power supply;

an electrically insulated rigid end cap having a circumferential groove for receiving the open end of said glass tube, said end cap being secured to said glass tube with at least one liquid sealant; and an elongated conducting terminal having a first portion extending through said end cap and configured for electrical connectivity with a second conducting terminal of said power supply, and a second portion extending into said glass tube and configured for electrical connectivity with said cathode.

2. The ionization tube of claim 1, wherein said cathode is cylindrically shaped and fabricated from stretch aluminum metal.

3. The ionization tube of claim 1, wherein said anode is cylindrically shaped and fabricated from stainless steel.

4. The ionization tube of claim 1, wherein the second portion of said elongated conducting terminal comprises a conductive current distributor member for providing current to said cathode.

5. The ionization tube of claim 4, wherein said conductive current distributor member includes a plurality of tines for contacting said cathode.

6. The ionization tube of claim 1, wherein one of said at least one sealant is provided along said circumferential groove and the open end of said glass tube.

7. The ionization tube of claim 6, wherein said sealant along said circumferential groove and the open end of said glass tube comprises a two-part epoxy sealant applied at the circumferential groove.

8. The ionization tube of claim 1, wherein one of said at least one sealant is provided along a peripheral edge of said end cap and the exterior surface proximate the open end of said glass tube.

9. The ionization tube of claim 8, wherein said sealant along said peripheral edge of said end cap and the exterior surface comprises a silicon rubber sealant.

10. The ionization tube of claim 1, wherein the open end of said glass tube includes a periphery having a rounded edge.

11. The ionization tube of claim 1, wherein said at least one sealant is flexible to permit expansion and contraction between said glass tube and end cap at temperatures exceeding 140 degrees F.

12. Method of fabricating a bipolar ionization tube, comprising:

providing a cylindrical glass tube that is formed with an open end and closed end, the open end being annealed to form a rounded or beveled peripheral edge;

providing an electrically insulated rigid end cap having a circumferential groove sized to receive a peripheral edge of the open end of said glass tube;

providing a conducting terminal having a current distributor and a cathode lead;

inserting a wire mesh cylindrical cathode into said glass tube;

attaching a lower end of said conducting terminal to said end cap;

positioning said glass tube over said conducting terminal and seating the peripheral edge of the open end of said glass tube on the circumferential groove; and positioning a cylindrical anode over said glass tube; and wherein said end cap is secured to said glass tube with at least one sealant.

13. The method of claim 12, wherein said providing a conducting terminal includes the steps of fastening the current distributor to an upper end of the cathode lead.

14. The method of claim 12, wherein said cylindrical anode is a stainless-steel mesh anode and said cylindrical cathode is a stretch aluminum metal cathode.

15. The method of claim 12, wherein said attaching a lower end of said conducting terminal to said end cap includes the steps of:

inserting a power input terminal through a bore formed in a bottom portion of said end cap; and fastening a lower end of said cathode lead to an upper end of said power input terminal.

16. The method of claim 15, further comprising providing a first sealant in the bore prior to said inserting a power input terminal through the bore formed in a bottom portion of said end cap.

17. The method of claim 12, further comprising providing a second sealant in the circumferential groove prior to said positioning said glass tube over said conducting terminal and seating the peripheral edge of the open end of said glass tube on the circumferential groove.

18. The method of claim 12, wherein prior to said positioning a cylindrical anode over said glass tube, the method further comprises the step of providing a third sealant around a joint formed by a peripheral edge of the end cap and an adjacent wall of said glass tube.

* * * * *